Figure 1:
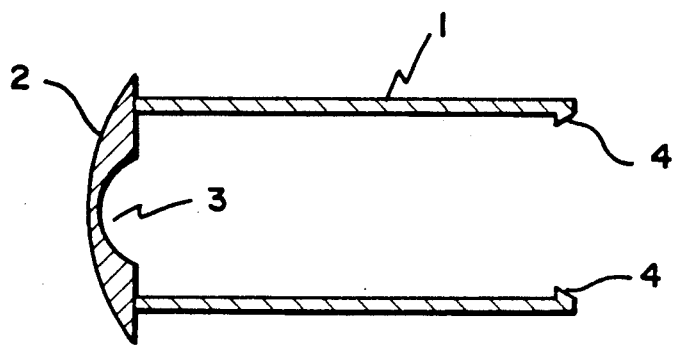

United States Patent [19]
Kohler

[11] Patent Number: 5,019,046
[45] Date of Patent: May 28, 1991

[54] SINGLE USE SYRINGE

[75] Inventor: Reinhard Kohler, Munich, Fed. Rep. of Germany

[73] Assignee: Inter System Verfahrenstechnik GmbH, Fed. Rep. of Germany

[21] Appl. No.: 465,781

[22] Filed: Mar. 29, 1990

[30] Foreign Application Priority Data

Jan. 19, 1989 [DE] Fed. Rep. of Germany ....... 3901484

[51] Int. Cl.⁵ ............................................. A61M 5/00
[52] U.S. Cl. .................................... 604/110; 604/218
[58] Field of Search ......................... 604/110, 187, 218

[56] References Cited

U.S. PATENT DOCUMENTS 4,880,410 11/1989 Rossmark ............................ 604/110

FOREIGN PATENT DOCUMENTS 210386 6/1984 Fed. Rep. of Germany ...... 604/110
2606643 5/1988 France ................................. 604/110

Primary Examiner—John D. Yasko
Attorney, Agent, or Firm—Sixbey, Friedman, Leedom & Ferguson

[57] ABSTRACT

Single use syringe which self-destructs in one-time use, precluding reuse thereof. The single use syringe consists of a barrel and a piston slideably arranged therein, the piston comprising two parts, namely, a cylindrical hollow body 1 and, arranged therein, a plunger 5 which at its front side carries a punch 6 that faces the front wall 2 of hollow part 1. During the injection process, the front wall 2 of the cylindrical hollow body 1 is pierced by punch 6, so that any attempt to draw up the previously used single use syringe again would cause the space in the barrel to draw air through the opening formed by the punch in the front wall 2 of cylindrical hollow body 1.

7 Claims, 2 Drawing Sheets

SINGLE USE SYRINGE

The invention relates to a single use syringe having a barrel at which there is provided an (injection) needle, in which barrel a piston is arranged that is sealingly slidable, relative thereto.

Such a syringe is used, for example, for injecting medications and other matter into parts of the human body, like, for instance, a vein.

For considerations of hygiene, as well as for reasons of avoiding transferring of a disease, it is necessary to sterilize a syringe after each use before using it again. Due to the fact that generally the ability to sterilize to the degree required is not available to the average person, those individuals rely on so-called single use syringes which are intended for single use only and thereafter are to be discarded.

However, it frequently happens that even single use syringes are purposely, or accidentally, reused without proper sterilization between repeat usage.

When two different persons, one after the other, use the same single use syringe without sterilizing it between usage, there is the danger of transferring pathogenic material from one person to the other. Consequently, such multiple use of single use syringes should be avoided under all circumstances, and should, more importantly, even be prevented.

Accordingly, it is the objective of the invention to provide a single use syringe of the kind described above, in which the possibility of multiple us is eliminated.

Accordingly, the single use syringe of the invention has a design, such that it self-destructs during use, due to the fact that during the injection, the punch of the plunger pierces the face wall of the cylindrical body, thus destroying the tight seal of the space between the barrel and the piston, necessary for the drawing up of the syringe, thereby preventing a repeated drawing up of the syringe and subsequent reuse thereof.

Figure 2:
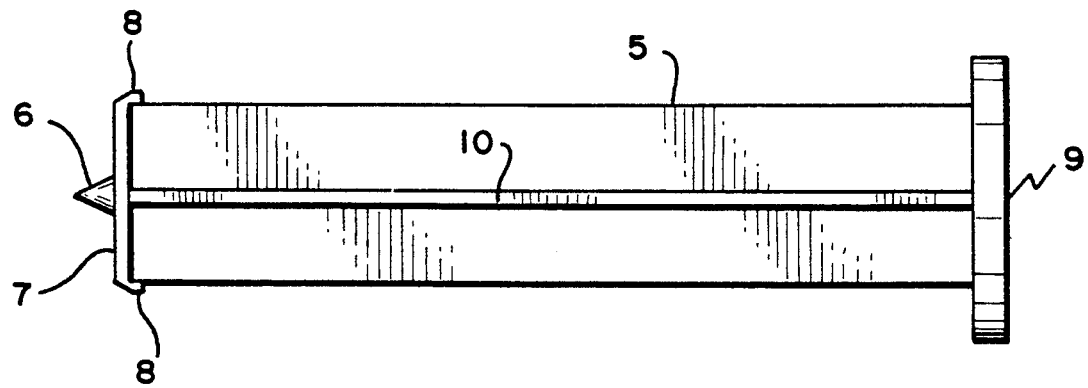
Figure 3:
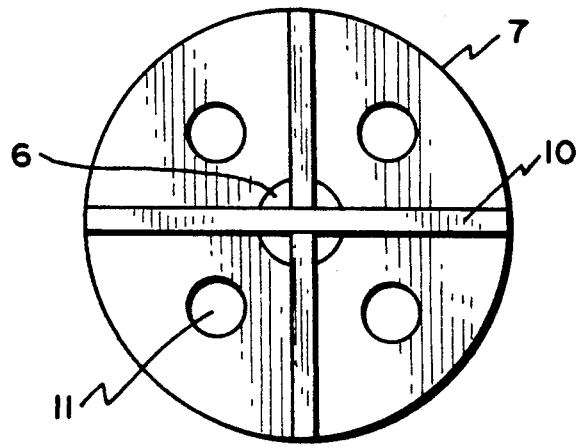
Figure 4:
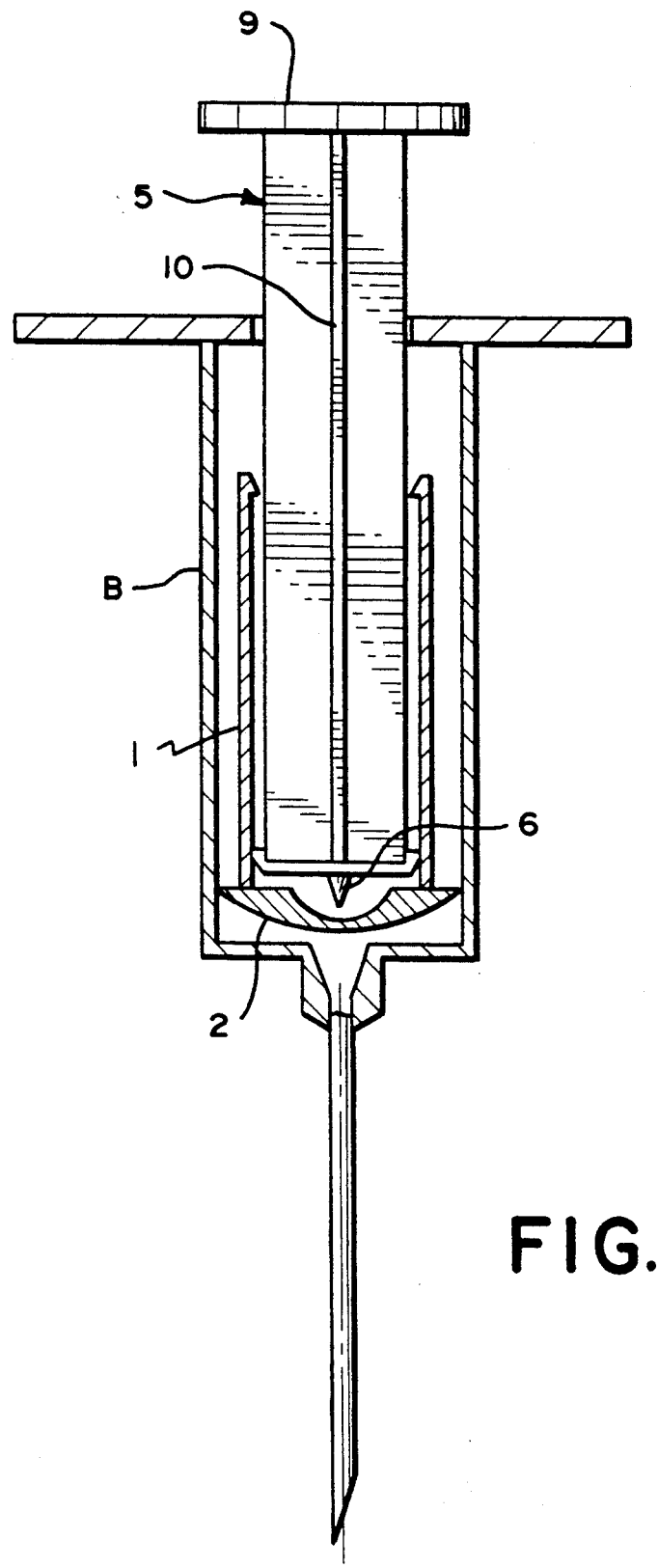

The invention is further illustrated by the following example by way of a drawing, which shows:

FIG. 1 a cross sectional view of a cylindrical hollow body of the inventive single use syringe FIG. 2 a partial cross sectional lateral view of the associated plunger FIG. 3 a view onto the front plate of the plunger, viewed from the side which is facing away from the punch, and FIG. 4 a cross-sectional view of the FIG. 2 position within the FIG. 1 barrel which, in turn, is within the barrel of a syringe.

The depicted piston of the single use syringe consists of two main parts, i.e. a cylindrical hollow body 1, shown in FIG. 1, and a plunger 5, shown in FIGS. 2 and 3.

The cylindrical hollow body 1, depicted in FIG. 1, is open at one end and is sealed at the other end by a front wall 2 whose diameter is somewhat larger than the outer diameter of the cylindrical hollow body 1. Facilitated by the shoulders thus formed, front wall 2 of cylindrical hollow body 1 sealingly contacts the inner wall of the barrel B of the syringe (FIG. 4) to provide a tight sealing of the space between the barrel and the piston, i.e. the cylindrical hollow body 1, which is necessary for drawing up of the syringe.

The front wall 2 of cylindrical hollow body 1 has a configuration such that it is weaker in its mid-section than at its outer periphery, a configuration which can be achieved, for instance, by having a concave recess 3 in the mid-section at the inner side of the front wall 2. Preferably, front wall 2 has an outward curve, and concave recess 3 has a smaller radius of curvature than that outward curve, resulting in the desired degree of taper. The weakening of front wall 2, may, however, also be achieved in other ways, like, for instance, by convex recesses at the outer side, steplike clearances, etc.

As depicted in FIGS. 2 and 4, associated plunger 5, disposed in the interior of cylindrical hollow body 1, is in the form of a cross-piece 10, a configuration which is commonly used for single use syringes. Plunger 5 has a cross-like cross-sectional configuration and has a front plate 7 at one end that is dimensioned such that it essentially fills the cross sectional area of cylindrical hollow body 1. At the other side of cross-piece 10, there is a contact plate 9 whose outer diameter, preferably, is larger that the outer diameter of the barrel, facilitating an easy manual actuation of plunger 5 at contact plate 9.

At its outer side, front plate 7 of plunger 5 has a punch 6 in the center and is provided with openings 11, in a manner depicted in FIG. 3, via which the space between the outer side of front plate 7 and the inner side of front wall 2 of cylindrical hollow body 1 is connected with outside air.

At the inner surface of cylindrical hollow body 1, at its open end, as well as at the outer edge of front plate 7 of plunger 5, there are locking devices 4, 8 in the form of ring-like shoulders, with mutual complementary configuration. These locking devices 4 jointly form a spring lock.

The cylindrical hollow body 1, as well as plunger 5, respectively, may be manufactured as one-unit injection molded parts of the same plastic material, e.g. PVC, whereby punch 6 also may be formed as a one-piece unit with plunger 5.

The following is a description of the operating mode of the above example, with reference to the inventive single use syringe:

In assembled state, plunger 5 is arranged in cylindrical hollow body 1, while cylindrical hollow body 1 is disposed inside the barrel, B. The placement of plunger 5 into cylindrical hollow body 1 does not present any problems due to their elasticity, which is characteristic of these parts, and the fact that the blocking action of locking devices 4, 8, only, must be overcome. This action can be further facilitated by providing a corresponding inclined plane arrangement of shoulders 4 and 8.

When drawing up the syringe, plunger 5 initially is retracted by means of contact plate 9 up to that point where locking devices 8, provided at front plate 7, engage locking devices 4 inside cylindrical hollow body 1. A further retraction of plunger 5 causes cylindrical hollow body 1 to be taken along, thereby suctioning the material to be injected, into the barrel. This actual suction process, accordingly, is the same as that of the drawing up of a conventional single use syringe.

After the syringe has been drawn up and the injection is about to occur, the residual air volume in the needle tube is removed, as is customary, in that a small amount of the material to be injected is ejected. To this end, plunger 5 is again slid in the direction of front wall 2 of cylindrical hollow body 1 by means of contact plate 9, causing the air between these components to escape via openings 11 in front plate 7 of plunger 5. At the end of this feed movement, punch 6 reaches the inner surface of front wall 2 of cylindrical hollow body 1. A further advance movement of plunger 5 by way of contact plate 9, causes punch 6 to penetrate front wall 2 of cylindrical hollow body 1, piercing it. Subsequently, the outer surface of front plate 7 comes into contact with the inner surface of front wall 2. It presents no design difficulties to select the configuration such that the front wall 2 is sealingly penetrated by punch 6, thereby preventing the material to be injected from escaping from the interior of the barrel.

A still further advance of plunger 5, by way of contact plate 9, causes hollow body 1, seated thereon, whose front wall 2 has been pierced by punch 6 to be advanced in the barrel, causing a certain amount of the material to be injected to be expelled, as is the case with conventional syringes. Thereafter, the (syringe) needle can be inserted, and by further advancement of the piston, consisting of cylindrical hollow body 1 and plunger 5, the injection can be carried out.

An appropriate selection of material and a corresponding design of punch 6 of plunger 5, as well as of front wall 2 of cylindrical hollow body 1, ensures that the penetration pressure, i.e. that pressure which is necessary for punch 6 to penetrate front wall 2, is lower than the pressure necessary for the injection itself, with the result that punch 6 pierces front wall 2 prior to the actual injection process.

Consequently, due to the fact that prior to, or not later than during the injection process, front wall 2 of cylindrical hollow body 1 is pierced by punch 6 and thereby is destroyed, the syringe cannot be reused after a single use injection. In an attempt to draw up the previously used syringe, the space in the barrel would pull in air due to the opening created by punch 6 in front wall 2 of cylindrical hollow body 1. Accordingly, at minimum, an unintentional reuse of the single use syringe is not possible.

Parts List

1. Cylindrical hollow body
2. Front wall
3. Recess
4. Locking device
5. Plunger
6. Punch
7. Front plate 7
8. Locking device
9. Contact plate
10. Cross-piece
11. Openings

I claim:

1. Single use syringe having a barrel, at which there is provided a needle, and in which a piston is arranged, which is sealingly slideable, relative thereto, wherein the piston comprises a cylindrical hollow body which is open at one end and is closed at on opposite end by a front wall which is weaker in its mid-section that at its peripheral area and a plunger which is arranged in the cylindrical hollow body in a slideable manner relative thereto, said piston having a punch on a front plate at a center part thereof that faces the weaker midsection of the front wall of the cylindrical hollow body, wherein a locking device is provided for holding the plunger within the cylindrical hollow body when the plunger is at a distance from the front wall of the cylindrical hollow body; wherein a space is formed between the front wall of the cylindrical hollow body and the front plate of the plunger; and wherein the front plate of the plunger essentially spans the cross sectional area of the cylindrical hollow body and has at least one opening through which said space between the front wall of cylindrical hollow body and front plate is connected to outside air; whereby said front plate is punctured by said punch during injection and the ability for fluids to be aspirated by said syringe thereby destroyed.

2. Single use syringe according to claim 1, characterized in that the locking device 4,8 consists of two shoulders having a mutually complementary configuration, which shoulders, respectively, are provided at the inner surface of cylindrical hollow body and at an outer edge of front plate of the plunger.

3. Single use syringe according to one of the previous claims, wherein the plunger and the punch are of a one-piece configuration.

4. Single use syringe according to claim 3, wherein the plunger the punch, and the cylindrical hollow body, are injection-molded parts, made of the same plastic material.

5. Single use syringe according to one of claims 2 or 1, wherein said front wall of the hollow body is convexly curved at a side facing into said barrel and concavely curved recess at a side facing said plunger, the weakening of the front wall resulting from said concave recess having a smaller radius of curvature than that of the convexly curved side of the front wall.

6. Single use syringe according to claim 5, wherein said plunger has a cross sectional configuration and said at least one opening of the front plate comprises an opening between each of respective pairs of branches of said cross-like cross sectional configuration.

7. Single use syringe according to claim 1, wherein said plunger has a cross sectional configuration and said at least one opening of the front plate comprises an opening between each of respective pairs of branches of said cross-like cross sectional configuration.

* * * * *